United States Patent
Pechstein

(10) Patent No.: US 9,528,955 B2
(45) Date of Patent: Dec. 27, 2016

(54) INDUCTIVE CONDUCTIVITY SENSOR WITH A MULTI-PLY HOUSING

(71) Applicant: Endress + Hauser Conducta Gesellschaft für Mess-und Regeltechnik mbH + Co. KG, Gerlingen (DE)

(72) Inventor: Torsten Pechstein, Radebeul (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 297 days.

(21) Appl. No.: 14/103,080

(22) Filed: Dec. 11, 2013

(65) Prior Publication Data
US 2014/0167790 A1    Jun. 19, 2014

(30) Foreign Application Priority Data

Dec. 17, 2012    (DE) .................. 10 2012 112 388

(51) Int. Cl.
| | | |
|---|---|---|
| *G01R 27/08* | (2006.01) | |
| *G01N 27/02* | (2006.01) | |
| *G01N 27/06* | (2006.01) | |

(52) U.S. Cl.
CPC ............ *G01N 27/025* (2013.01); *G01N 27/06* (2013.01)

(58) Field of Classification Search
CPC ........... G01V 3/26; G01V 3/28; G01R 33/286; G01R 33/4808; G01R 27/22; G01R 33/34053; G01R 33/3657; G01R 33/34092; G01R 33/561; G01N 24/088; G01N 27/025; G01N 27/06; G01N 33/54333; G01N 27/023; G01N 27/07; G01N 33/206; H02J 7/025; H02J 17/00; H02J 5/005; G01F 23/20; G01F 23/24; G01F 23/245; G01F 23/26; G01F 23/263; G01F 23/36; G06K 19/0717
See application file for complete search history.

(56) References Cited

U.S. PATENT DOCUMENTS

| | | | |
|---|---|---|---|
| 3,090,910 A | * | 5/1963 | Moran ..................... G01V 3/28 324/221 |
| 8,531,018 B2 | | 9/2013 | Pahl |
| 2012/0098550 A1 | | 4/2012 | Fanselow et al. |

(Continued)

FOREIGN PATENT DOCUMENTS

| | | |
|---|---|---|
| CN | 2593202 Y | 12/2003 |
| CN | 101490512 A | 7/2009 |

(Continued)

OTHER PUBLICATIONS

Jan. 18, 2013 German Search Report, German Patent Office, Munich, Germany.

*Primary Examiner* — Vinh Nguyen
(74) *Attorney, Agent, or Firm* — Christopher R. Powers; PatServe

(57) ABSTRACT

An inductive, conductivity sensor comprising a transmitting coil, a receiving coil and, surrounding the transmitting coil and the receiving coil, a housing, which has, for immersion in a measured medium, at least one housing section, whose housing wall surrounds the transmitting coil and the receiving coil. The housing wall of the housing section surrounding the transmitting coil and the receiving coil has a multiply construction, which comprises at least a first ply of a first material and a second ply of a second material different of the first material.

10 Claims, 2 Drawing Sheets

(56) References Cited

U.S. PATENT DOCUMENTS

2012/0182027 A1* 7/2012 Jagiella .................. G01N 27/06
                                                            324/654
2013/0021042 A1* 1/2013 Lammel ................. G01R 27/22
                                                            324/654

FOREIGN PATENT DOCUMENTS

| DE | 102007008074 A1 | 8/2008 |
| DE | 102010012042 A1 | 9/2011 |
| DE | 102010042832 A1 | 4/2012 |
| WO | 2008098953 A1 | 8/2008 |

* cited by examiner

INDUCTIVE CONDUCTIVITY SENSOR WITH A MULTI-PLY HOUSING

TECHNICAL FIELD

The invention relates to an inductive, conductivity sensor and to a method for its manufacture.

BACKGROUND DISCUSSION

Inductive, conductivity sensors serve in a large number of applications in laboratory and process measurements technology for registering the conductivity of a liquid, measured medium. They are preferably used where large measuring ranges and high chemical or thermal loadings occur. This is true, for example, in a large number of industrial, chemical processes, however, also for hot steam sterilization methods, which are frequently applied in the foods technology field due to its associated high requirements as regards hygiene.

An inductive, conductivity sensor includes a transmitting coil and a receiving coil, which are, as a rule, embodied as ring coils, which are also referred to as toroidal coils. Such a conductivity sensor functions as a kind of double transformer, wherein the transmitting and receiving coils are inserted sufficiently far into the measured medium that a closed electrical current path can form extending through the measured medium and passing through the transmitting and receiving coils. When the transmitting coil is excited with an alternating voltage signal, it produces a magnetic field, which induces in the closed path through the medium and through the coils an electrical current, whose level depends on the electrical conductivity of the measured medium. Since this alternating electrical current in the medium brings about, in turn, a variable magnetic field surrounding it, an alternating electrical current is induced in the receiver coil. This alternating electrical current, respectively a corresponding alternating voltage, delivered by the receiver coil as output signal is a measure for the electrical conductivity of the measured medium.

For supplying the transmitting coil with an alternating voltage, an inductive, conductivity sensor includes a driver circuit connected with the transmitting coil. For registering the output signal of the receiving coil, the conductivity sensor includes, moreover, electrically connected with the receiving coil, a receiving circuit, which is embodied to output the registered measurement signal (which may, in given cases, be conditioned by the receiving circuit) to a sensor electronics, which serves to process the measurement signal further and, in given cases, to digitize it. Frequently, conductivity sensors are embodied as measuring probes at least sectionally immersible in the measured medium. Such a measuring probe includes a measuring probe housing, in which are accommodated the transmitting and receiving coils, and, in given cases, the driver circuit and the receiving circuit, as well as other circuit parts assembled with the transmitting and receiving circuit in a sensor circuit. The measuring probe is connected in such an embodiment with a remotely situated, superordinated unit, for example, a display unit, a measurement transmitter, or a computer. The superordinated unit can be embodied both for energy supply of the measuring probe as well as also for data communication with the measuring probe. The sensor circuit contained optionally in the measuring probe can be embodied to forward the further processed, in given cases, digitized, measurement signal to the superordinated unit. The corresponding measured value can be displayed via the superordinated unit by means of a display system or output via a data interface.

Inductive, conductivity sensors of this type are known, for example, from U.S. Pat. No. 3,603,873, DE 198 51 146 A1, DE 41 16 468 A1, DE 10 2006 025 194 A1 as well as DE 10 2006 056 174 A1.

Housings of inductive, conductivity sensors are manufactured, guided by the above-described principles of operation, such that the housing surrounding the transmitting and receiving coils does not form a closed, electrically conductive path. Therefore, preferably non-conductive materials are utilized for the housing. The coils of inductive, conductivity sensors can, in such case, be provided in different ways with a non-conductive housing formed, most often, of a plastic material. A known construction of an inductive, conductivity sensor includes, for example, a coil support body of metal, in which the transmitting and receiving coils are arranged, and which is surrounded with a non-conductive synthetic material, for example, with injection molded polyetheretherketone (PEEK). The coil support body serves to protect the coils against high injection pressures and high temperatures during injection molding and, in the subsequent operation of the sensor, to shield the transmitting and receiving coils against undesired direct couplings between the coils.

Described in German patent, DE 10 2010 042 832 A1 is an inductive, conductivity sensor having a plastic housing, which contains a coil component. The coil component includes a support plate, on whose front side the transmitting coil and on whose rear side the receiving coil are arranged coaxially relative to the rotational symmetry axes of the transmitting and receiving coils. The support plate includes an opening, which is aligned with oppositely lying openings of the plastic housing. A plastic sleeve, whose ends are connected sealed against the medium by ultrasonically welded connections with the openings of the plastic housing, is led through the opening of the support plate and passes also through the transmitting coil and the receiving coil. If the housing is immersed in a measured medium, the measured medium also passes through the sleeve and forms, thus, a path of medium passing through the coils, so that, such as above described, when the transmitting coil is excited with an alternating voltage, an electrical current flow is induced extending along a closed path through the measured medium. The welded connection between the sleeve ends and the openings of the housing means that the housing is sealed to media, so that the measured medium cannot penetrate into the housing and into the circuits, respectively the sensor electronics, contained in the housing.

The plastics used for housings of inductive, conductivity sensors must meet diverse requirements as regards workability, as well as chemical, mechanical, thermal, also optical properties. Moreover, plastics coming in contact with the measured medium must, depending on the character of the application, in which the sensor is to be applied, fulfill certain requirements as regards biocompatibility or, especially in the fields of the foods industry and the pharmaceuticals industry, be qualified for certain permits as regards their physiological compatibility, permits which must be granted, for example, by health officials. Thus, the scope of plastics suitable for the manufacture of the housing can be limited. Especially, there are no plastics, which have all the desired properties of the housing, so that for the material selection lastly a compromise must be explored. Thus, for example, the application of glass fiber reinforced plastics enables the cost effective manufacture of mechanically very stable housings, yet these materials are, most often, not allowable for use in the foods field. In the foods field, therefore, sensors of unreinforced, permitted materials, such as PEEK or perfluoroalkoxy polymers (PEA), must be applied, which have a lesser mechanical stability.

SUMMARY OF THE INVENTION

It is, therefore, an object of the invention, to provide an inductive, conductivity sensor and a method for its manufacture, which overcome these disadvantages. Especially, an inductive, conductivity sensor should be provided, whose construction allows an improved matching of the media-contacting housing to the most varied of requirements.

This object is achieved according to the invention by an inductive, conductivity sensor which includes a transmitting coil, a receiving coil and, surrounding the transmitting coil and the receiving coil, a housing, which has, for immersion in a measured medium, at least one housing section, whose housing wall surrounds the transmitting coil and the receiving coil, wherein the housing wall of the housing section surrounding the coils has a multi-ply construction, which comprises at least a first ply of a first material and a second ply of a second material different from the first material.

Since the housing coming in contact with the medium has a multi-ply construction with layers of different materials, the respective properties of the different materials can be combined with one another, in order so to provide, and to combine with one another, different desired properties of the housing. Consequently, no compromises must be made as regards desired housing characteristics.

The measuring probe housing of the inductive, conductivity sensor can be formed of a plurality of housing modules. A first housing module can comprise the housing wall surrounding the transmitting coil and the receiving coil, while a second housing module connected with the first housing module can contain at least parts of the sensor circuit. In this embodiment, the first housing module can have the described multi-ply construction, which includes at least a first ply of a first material and a second ply of a second material. The second housing module, which is not intended for contact with the measured medium, can likewise have a multi-ply construction. It can, however, also be formed in conventional manner of a single material.

In an embodiment, the first and second plies, especially all plies, of the multi-ply construction of the housing wall are formed of an electrically non-conductive material.

Preferably, the first material effects a first desired property of the housing, while the second material effects a second property of the housing different from the first property.

A first desired property of the housing can be, for example, a high mechanical stability and/or a good mechanical processability. In this case, suitable as material of a first ply is, for example, a relatively highly crosslinked polymer, such as, for example, a thermosetting or a thermoplastic material, or also a ceramic material.

A second desired property of the housing can be, for example, a high chemical reaction inertia, which means that the housing is not chemically attacked by substances contained in the measured medium. A therewith related, desired property is an acceptance of the housing material in the field of hygienic, for example, biotechnological, pharmaceutical or food, applications.

Used in these cases as material of a media-contacting ply is, for example, a suitable glass or ceramic material or a suitable chemically inert polymer, such as, for example, PFA, PTFE or PEEK.

A third desired property of the housing can be, for example, a high water diffusion resistance, which prevents water from an aqueous measured medium from penetrating through the housing wall into the interior of the housing and attacking the coils or the sensor circuit, respectively causing a short circuit. For increasing the water diffusion resistance of the housing, a layer of the housing can be formed of a glass, a ceramic inorganic material or a plastic with lesser water retention capability, such as, for example, parylene or polyimide.

Additionally, a ply, especially the media contacting ply, can be formed of a biocidal material, e.g. of a biocidal plastic or a plastic with biocidally acting inclusions, inclusions such as, for example, silver nano particles.

Other properties adjustable by way of a corresponding selection of materials for the plies forming the housing include temperature stability, good processability with an injection molding method, respectively a good workability of the injection molded product, antifouling properties and wettability.

A functional layer based on a hybrid polymer also represents an option for providing a desired housing property. Such hybrid polymeric materials can be, for example, organically modified polysiloxanes, which can result from a sol gel process. Basic building blocks of such hybrid polymers can include, besides tetraalkoxysilanes, organically modified alkoxy silane compounds of the type $RSi(OR)_3$ or $R_2Si(OR)_2$. Depending on the substituent R, these can function within the silicate matrix as organic network formers or network transformers. Layers based on such hybrid polymers can, depending on composition and/or degree of crosslinking, respectively manufacturing process, provide various functions, such as e.g. increasing mechanical and chemical durability of the housing. They can also serve as barrier layers against water or other undesired substances.

The choice of material of the multi-ply construction can, moreover, take into consideration that the combined materials cling well to one another or by means of tackifiers durably bond with one another. Along with that, it is advantageous, when the thermal coefficients of expansion differ by no more than 10-50 ppm/K. The allowable differences of the thermal coefficients of expansion depend, in such case, also on the respectively selected thicknesses of the individual plies.

In an embodiment of the conductivity sensor, such can have, connected with the multi-ply construction or integrated into the multi-ply construction, an electrically conductive, for example, metal, ply, which is embodied in such a manner that no closed, electrically conductive path results around the transmitting and/or receiving coil. This ply can be formed, for example, by a coil support body of metal, in which the coils are embedded. Alternatively, the electrically conductive ply can be implemented as an additional ply of the multi-ply construction.

The different plies of the multi-ply construction can be arranged directly on top of one another. Alternatively, bonding promoting layers can be arranged between the plies.

In an advantageous embodiment, the first ply is composed of a glass fiber reinforced thermoplastic and the second ply, especially the ply contacting media during measurement operation, of a fiber free thermoplastic. The first ply provides the housing with a very good mechanical stability. Housing plies of thermoplastic materials can, moreover, be produced very well by means of an injection molding method and are, consequently, simple and favorable to manufacture. This is true both for the fiber reinforced first ply as well as also for the media contacting, second ply. Since the media contacting, second ply is composed of a fiber free plastic, the conductivity sensor with this housing can also be applied in food technology processes, even though the glass fiber containing material of the first ply would otherwise not be allowed in food technology processes.

In another advantageous embodiment, which also is combinable with the above mentioned embodiment, the multi-ply construction of the housing wall can comprise at least one ply of a material forming a diffusion barrier for water, especially parylene or polyimide. This ply can be one of the already mentioned first or second plies or an additional ply of the multi-ply construction.

Alternatively, the multi-ply construction of the housing wall can comprise at least one ply of an inorganic material, especially a ceramic or a glass-like material. Again, this ply can be one of the already mentioned first or second plies or an additional ply of the multi-ply construction.

In an additional alternative embodiment, at least one ply of the multi-ply construction of the housing wall can comprise a hybrid polymer, especially an organically modified siloxane. This ply can be one of the already mentioned first or second plies or an additional ply of the multi-ply construction.

The multi-ply construction can, thus, comprise two or more plies of the most varied of combinations of the materials mentioned here or other materials.

The transmitting coil and the receiving coil can be embodied as toroidal coils, wherein the housing section surrounding the coils is embodied in such a manner that the toroidal coils, upon immersion of the housing section into the measured medium, are traversed by a closed path through the measured medium. For this, the housing section can form a duct passing through the toroidal coils at least sectionally along a central axis of the toroidal coils extending perpendicularly to the winding advance of the toroidal coils, especially a rotational symmetry axis of the toroidal coils.

The method of the invention for manufacture of an inductive, conductivity sensor, especially according to one of the above described embodiments, includes steps as follows:

providing a sensor module, which includes the transmitting coil and the receiving coil as well as a housing of a first material, especially a material comprising a plastic, surrounding the transmitting and receiving coils, and coating at least one surface of the housing with at least one ply of a second material different from the first material.

The sensor module with the plastic housing of the first material can be formed, for example, by injection molding the first material around the transmitting and receiving coils. For protecting the coils from high temperatures and mechanical loadings arising during the injection molding, they can be accommodated in a coil support body (such as described in DE 2007 039 015 A1), which remains in the plastic housing produced by the injection molding around the coil support body.

In an alternative embodiment, the sensor module of the first material can be formed by introducing the transmitting and receiving coils, arranged on a support plate on both sides of, and surrounding, an opening of the support plate, into a housing of the first material, wherein a sleeve likewise of the first material is inserted through a first cavity of the housing through the opening of the support plate into the housing and a first end of the sleeve is connected with the first cavity of the housing by material bonding, e.g. by welding or adhesive. The other end of the sleeve is connected by material bonding with a second cavity of the housing lying opposite the first cavity. The so formed sensor module can then be coated with the second material.

The above mentioned method step of coating the housing, which can be, for example, a plastic housing, can comprise a CVD deposition method for producing a ply of a second plastic.

The step of coating the housing can alternatively comprise a PVD or plasma coating method for producing a ply of an inorganic material, especially a ceramic or a glass-like material. The inorganic layer material can be, moreover, also a metal. In this case, the ply is to be applied such that no closed, electrically conductive path results around the transmitting and/or receiving coils.

The coating of the plastic housing can comprise, supplementally or alternatively, also a lacquering method, especially an applying by means of an immersion- or spray coating method, a doctor blade deposition, a spin-on deposition method, a roller application or a microspray deposition with a subsequent curing by thermal treatment or UV irradiation.

The coating of the housing can comprise a step of injecting a plastic around the housing.

The housing, in the step of coating, can be coated simultaneously on an outer surface and on an inner surface facing away from the outer surface.

BRIEF DESCRIPTION OF THE DRAWINGS

The invention will now be described in greater detail based on examples illustrated in the drawing, the figures of which show as follows.

DETAILED DISCUSSION IN CONJUNCTION WITH THE DRAWINGS

Figure 1:
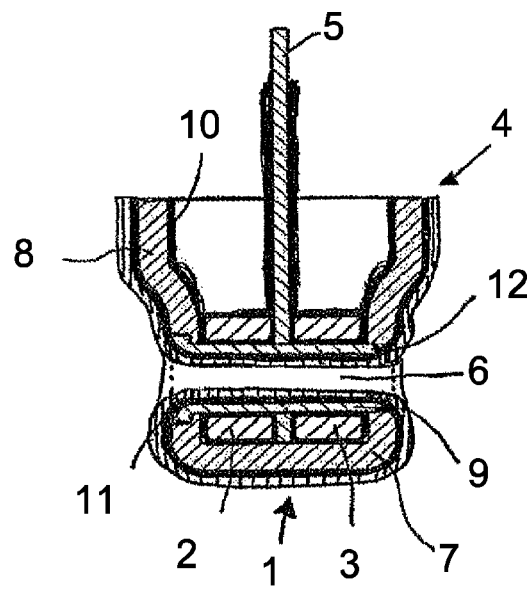
FIG. 1 is a sensor module of a first inductive, conductivity sensor having a housing, which has a multi-ply construction.

FIG. 1 shows a sensor module 1 of an inductive, conductivity sensor having a transmitting coil 2 and a receiving coil 3, which are accommodated in a housing 4. The transmitting coil and the receiving coil 3 are arranged lying opposite one another and facing away from one another on the faces of a circuit card 5. The transmitting and receiving coils embodied as rotationally symmetric toroidal coils are, in this way, arranged lying coaxially one after the other. Circuit card 5 includes, for contacting the coils, conductive traces (not shown), which connect the transmitting coil 2 with a driver circuit and the receiving coil 3 with a receiving circuit. The driver circuit and the receiving circuit can be components of a sensor circuit arranged on the circuit card 5.

Housing 4 forms a duct 6 passing through the transmitting coil 3 and the receiving coil 3 along their axes of rotation. If the housing 4 is immersed in an electrically conductive, measured medium, such surrounds the housing 4 and penetrates into the duct 6, so that, as explained above, there can form in the measured medium a closed electrical current path passing through the two coils, when the transmitting coil 2 is excited with an alternating voltage.

Housing 4 has a multi-ply construction of four separate plies. A first ply 7 is formed of glass fiber reinforced PEEK. This material exhibits a high mechanical stability and is relatively simple to manufacture by means of an injection molding method. Moreover, glass fiber reinforced PEEK can be processed as needed. Especially, individual PEEK components can be connected with one another. For instance, in the example shown here, a first housing part 8 can be connected liquid tightly with a sleeve 9 by ultrasonic welding.

First ply 7 is coated on its surface facing the housing interior with a second ply 10 and on its outer surface with a third ply 11. In the example described here, second ply 10 and third ply 11 are made of parylene, which serves as a diffusion barrier against water. Such a diffusion barrier is advantageous in combination with a first ply of PEEK or other plastic material possessing at high temperatures a non-negligible water retention ability. Equally suitable as diffusion barriers are also other hydrophobic plastics, e.g. polyimide.

Second ply 10 of parylene forms in the example shown here not only the housing inner wall of the housing 4, but also covers the coils and the circuit card 5 arranged in the housing 4, including the conductive traces and circuit parts arranged on the circuit card 5, and offers, thus, additional protection against moisture penetrating into the housing interior.

Arranged over the third ply 11 is a fourth ply 12 of PEEK. PEEK is physiologically unobjectionable and chemically inert toward a large number of possible measured media. Such material is, consequently, suitable as media contacting material for a large number of potential measured media and, consequently, quite suitable as outer layer of the housing 4.

The multi-ply construction 4 brings together for the housing of a conductivity sensor, thus, a number of desirable properties, whose combination would not be attainable by means of a single plastic material or perhaps attainable only in the face of high cost: First, the housing is mechanically stable and manufacturable with established and cost effective methods. Second, diffusion of water into the housing interior is resisted. Third, the housing has, serving for contact with the measured medium, a surface of a physiologically unobjectionable material suitable for hygienic applications, e.g. in the foods field.

The sensor module 1 shown in FIG. 1 can be produced in the following manner: The circuit card 5 populated with the transmitting coil 2, the receiving coil 3 and, in given cases, additional circuit parts is, in a first step, installed in a housing part 8 of glass fiber reinforced PEEK. The transmitting coil 2 and the receiving coil 3 are so arranged on the circuit card 5 that they surround an opening in the circuit card 5. The housing part 8 can be manufactured, for example, by means of an injection molding method. The housing part includes two oppositely lying cavities, which align with the opening in the circuit card 5 surrounded by the toroidal coils. A sleeve 9 of PEEK or glass fiber reinforced PEEK is led through a first cavity of the housing part 8 and through the therewith aligned opening in the circuit card 5, and an end of the sleeve 9 is connected with the first cavity by an encircling ultrasonic welding. The opposite end of the sleeve is, by a surrounding ultrasonic welding, correspondingly connected with the second cavity of the housing part lying opposite the first cavity. In this way, a duct 6 is formed, which extends axially relative to the rotational axis of the transmitting and receiving coils 2, 3. During measurement operation, measured medium flows through duct 6.

In a second step, the housing of glass fiber reinforced PEEK serving as first ply 7 of the housing 4 and formed of the housing part 8 and the sleeve 9 is coated on both sides with parylene. The parylene coating can be produced, for example, by means of a CVD method. In the present example, not only the inner and outer walls of the housing formed of the housing part 8 and the sleeve 9 are coated for producing the second and third plies 10, 11 of the housing 4, but, instead, also the coils and the circuit card including, in given cases, circuit parts arranged thereon, to the extent that these are accessible from the gas phase.

In a third step, the third ply 11 of the housing 4 formed of parylene is provided with an additional coating 12 of PEEK. This can occur by means of an injection molding method.

Other, especially bonding promoting, intermediate plies can be provided between the four plies shown in FIG. 1.

Figure 2:
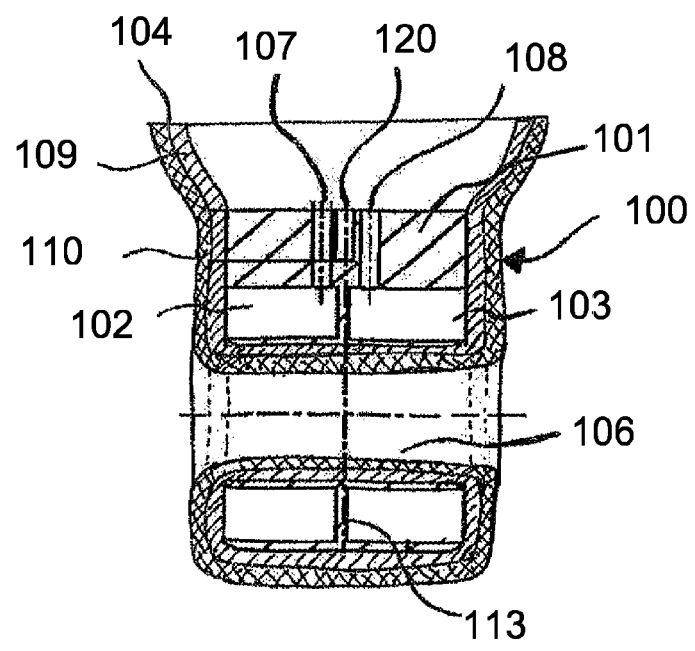
FIG. 2 is a sensor module of a second inductive, conductivity sensor having a housing, which has a multi-ply construction.

FIG. 2 shows a second example of a sensor module 100 of an inductive, conductivity sensor.

Sensor module 100 includes a coil support body 101 having an annular transmitting coil chamber, in which is arranged a transmitting coil 102 embodied as a toroidal coil, and an annular receiving coil chamber, in which is arranged a receiving coil 103 embodied as a toroidal coil. Coil support body 101 forms, passing through the transmitting coil 102 and the receiving coil 103 arranged coaxially behind the transmitting coil 102, a sleeve-shaped duct 106, which serves to form during measurement operation a section of a closed media path passing through the coils. Upon excitation of the transmitting coil 102 with an alternating voltage a closed electrical current path can be induced in the media path. Coil support body 101 can be of metal, for example.

Coil support body 101 includes first connection bores 107, through which connection lines of the transmitting coil 102 extend, as well as second connection bores 108, through which connection lines of the receiving coil 103 extend. Additionally, the coil support body 101 has a groove 120, in which a circuit card (not shown) can be arranged, on which the sensor circuit having a driver circuit connected with the connection lines of the transmitting coil 102 and a receiving circuit connected with the connection lines of the receiving coil 103 are arranged.

Coil support body 101 and the circuit card applied in the groove 120 are surrounded by a housing 104. Housing 104 has a multi-ply construction comprising two plies.

The first ply 109 is composed of a plastic, e.g. PEEK or PFA, which is applied by injection molding around and onto the coil support. The second ply 110 is composed of a glass-like or ceramic, inorganic material, e.g. in the present example, $Al_2O_3$, applied onto the first ply by means of a PVD- or plasma coating method. Such is chemically highly resistant and acts as a diffusion barrier against penetration of water into the housing interior.

Housing 104 possesses, thus, due to the different, housing materials combined with one another, the following properties: First of all, the housing 104 is mechanically stable and manufacturable by means of well manageable, known and price favorable manufacturing methods, namely injection molding and PVD. Second, the media contacting, outer wall of the housing is chemically inert relative to a large number of possible measured media. Third, penetration of water into the housing interior due to the water retention ability of a plastic (e.g. PEEK or PFA) forming the housing is suppressed by means of the $Al_2O_3$ ply serving as diffusion barrier.

In an additional example of an embodiment (not shown), a housing with a greater number of plastic plies is provided, which is manufactured by a corresponding number of injecting molding procedures.

Instead of PEEK or glass fiber reinforced PEEK, of course, other suitable, preferably thermoplastic, in given cases, fiber reinforced, plastic-materials can be used for one or more plies of a housing. Examples include acrylonitrile butadiene styrene (ABS), polyamides (PA), polylactate (PLA), polymethylmethacrylate (PMMA), polycarbonate (PC), polyethylene terephthalate (PET), polyethylene (PE), polypropylene (PP), polystyrene (PS), polyvinyl chloride (PVC) as well as perfluoroalkoxy polymers (PFA).

Figure 3:
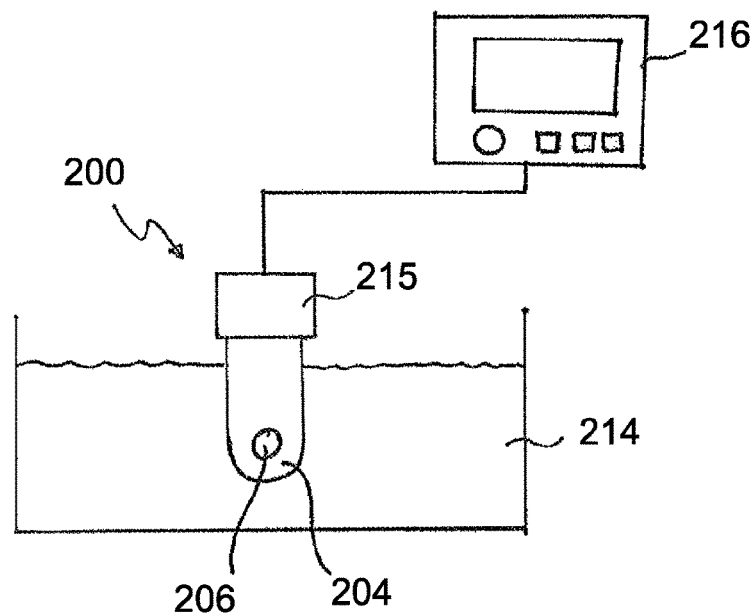
FIG. 3 is an inductive, conductivity sensor during measurement operation.

FIG. 3 shows schematically a conductivity sensor 200 having a first housing module 204 intended for immersion in a measured medium 214 and a second housing module 215 affixed thereto. Accommodated in the first housing module 204 are the transmitting and receiving coils, as well as, in given cases, at least parts of the driver circuit exciting the transmitting coil with an alternating voltage and at least parts of the receiving circuit connected with the receiving coil for registering and conditioning a signal induced in the receiving coil as a function of the conductivity of the measured medium 214. The first housing module 204 has a duct 206 passing through coils contained in the first housing module 204. Measured medium 214 flows through duct 206, when the housing module 204, such as shown in FIG. 3, is immersed in the measured medium 214. Measured medium 214 can be located in a container, especially in a pipe or in a reaction vessel, in a manufacturing plant. Conductivity sensor 200 is, in such case, held in a retractable assembly installed in the pipe-, respectively vessel, wall, and is immersed in the measured medium 214 contained in the pipe or vessel.

The sensor circuit contained in the second housing module 215 is connected via a cable connection with a superordinated unit, which is, in the present example, a measurement transmitter 216. The superordinated unit can also be a computer or a programmable logic controller. The connection between the conductivity sensor 200 and the superordinated unit can also be a wireless connection. In this case, the superordinated unit can also be a portable device, especially an Internet- or radio capable telephone, such as a smart phone. The superordinated unit serves for supplying the sensor- and the driver circuit with energy, as well as for registering and additional processing, especially also for display, of the measured values registered by the conductivity sensor 200.

The first housing module 204 coming in contact with the measured medium 214 has a multi-ply construction of the invention, for example, as described in one of the above examples of embodiments. Since the second housing module 215 does not, as a rule, come in contact with the measured medium, it can be formed of any plastic. It can, however, also equally have a multi-ply construction, same as the first housing module 204.

The invention claimed is:

1. An inductive, conductivity sensor comprising:
    a transmitting coil;
    a receiving coil; and
    a housing surrounding said transmitting coil and said receiving coil, said housing has, for immersion in a measured medium, at least one housing section, whose housing wall surrounds said transmitting coil and said receiving coil, wherein:
    said housing wall of said housing section surrounding said transmitting coil and said receiving coil has a multi-ply construction, which comprises at least a first ply of a first material and a second ply of a second material different from said first material.

2. The inductive, conductivity sensor as claimed in claim 1, wherein:
    said first and said second plies, especially all plies, of the multi-ply construction of said housing wall are formed of an electrically non-conductive material.

3. The inductive, conductivity sensor as claimed in claim 1, wherein:
    said first ply is composed of a glass fiber reinforced thermoplastic and said second ply, especially an outer ply, is composed of a fiber free thermoplastic.

4. The inductive, conductivity sensor as claimed in claim 1, wherein:
    the multi-ply construction of said housing wall includes at least one ply of a material, especially parylene or polyimide, forming a diffusion barrier for water.

5. The inductive, conductivity sensor as claimed in claim 1, wherein:
    the multi-ply construction of said housing wall includes at least one ply of an inorganic material, especially a ceramic or a glass material.

6. The inductive, conductivity sensor as claimed in claim 1, wherein:
    the multi-ply construction of said housing wall includes at least one ply of a hybrid polymer, especially an organically modified polysiloxane.

7. The inductive, conductivity sensor as claimed in claim 1, wherein:
    the at least one ply is the first ply, the second ply or another ply of the multi-ply construction.

8. The inductive, conductivity sensor as claimed in claim 1, furthermore comprising:
    connected with the multi-ply construction or integrated into the multi-ply construction, at least one electrically conductive ply, which is embodied in such a manner that no closed electrically conductive path results around said transmitting and/or said receiving coil.

9. The inductive, conductivity sensor as claimed in claim 1, wherein:
    said transmitting coil and said receiving coil are embodied as toroidal coils; and
    said housing section is embodied such that said toroidal coils, upon immersion of said housing section into the measured medium, are surrounded by the measured medium to form a closed path through and around said toroidal coils.

10. The inductive, conductivity sensor as claimed in claim 1, wherein:
    said transmitting coil and said receiving coil are embodied as toroidal coils; said housing section forms a duct passing through said toroidal coils at least sectionally along a central axis of said toroidal coils, especially a rotational symmetry axis of said toroidal coils, extending perpendicularly to the winding advance of said toroidal coils.

* * * * *